United States Patent [19]
Budd et al.

[11] Patent Number: 5,423,228
[45] Date of Patent: Jun. 13, 1995

[54] DILUTION STACK SAMPLING APPARATUS

[75] Inventors: Allan L. Budd; William C. Knapp, both of Denver, Colo.

[73] Assignee: Monitor Labs, Inc., Englewood, Colo.

[21] Appl. No.: 992,584

[22] Filed: Dec. 18, 1992

[51] Int. Cl.$^6$ .............................................. G01N 1/22
[52] U.S. Cl. ............................. 73/863.21; 73/863.23; 73/863.43; 73/863.81; 73/864.73
[58] Field of Search ..................... 73/863.12–863.25, 73/863.41, 863.43, 863.81, 864.73, 864.74, 23.31, 28.04–28.06, 31.07, 863.83, 863.84

[56] References Cited

U.S. PATENT DOCUMENTS

| | | | |
|---|---|---|---|
| 3,046,791 | 7/1962 | Dinteren | 73/863.24 |
| 3,457,787 | 7/1969 | Maatsch et al. | 73/863.12 X |
| 3,512,393 | 5/1970 | Weiss | 73/863.24 X |
| 3,559,491 | 2/1971 | Thoen | 73/863.24 |
| 3,803,920 | 4/1974 | Homulya et al. | 73/864.34 |
| 3,817,100 | 6/1974 | Anderson et al. | 73/863.23 X |
| 4,004,882 | 1/1977 | Byrne et al. | 73/863.23 X |
| 4,452,068 | 6/1984 | Loo | 73/28.05 |
| 4,974,455 | 12/1990 | McGowan et al. | 73/863.12 |
| 5,078,758 | 1/1992 | Maller et al. | 73/864.81 X |
| 5,237,881 | 8/1993 | Ross | 73/863.12 |
| 5,297,432 | 3/1994 | Traina et al. | 73/863.23 X |

FOREIGN PATENT DOCUMENTS

| | | | |
|---|---|---|---|
| 2603948 | 9/1976 | Germany | 73/863.23 |
| 65133 | 5/1980 | Japan | 73/863.12 |
| 1113875 | 5/1968 | United Kingdom | 73/863.23 |
| 1496887 | 1/1978 | United Kingdom | 73/863.23 |
| 675342 | 7/1979 | U.S.S.R. | 73/863.12 |
| 1427213 | 9/1988 | U.S.S.R. | 73/863.23 |

*Primary Examiner*—Tom Noland
*Attorney, Agent, or Firm*—Fields, Lewis, Rost & Smith

[57] ABSTRACT

Dilution stack sampling apparatus, for analyzing gaseous components of a gas stream from a stack containing particulate material of varying size therein. A passageway has a first end communicating at an angle with the probe intermediate its ends to receive a sample of gas and to change its flow direction to inertially remove most of the particulate material. An eductor connected to the second end of the passageway mixes dilution air with the sample of gas to provide a diluted sample. A filter upstream of the second end of the passageway removes remaining particulate material from the sample of gas which is not the inertially separated. Instrument air can be provided in a back-flow direction at the upstream side of the filter to periodically remove particulate material from the filter. The diluted sample and the dilution gas are supplied to gas analyzer, and the mass flow rate of the dilution gas and diluted gas are measured. The amount of the dilution gas and the dilution sample are compared in the gas analyzer to determine the ratio of each measured gas in the sample to the total gas sample.

3 Claims, 4 Drawing Sheets

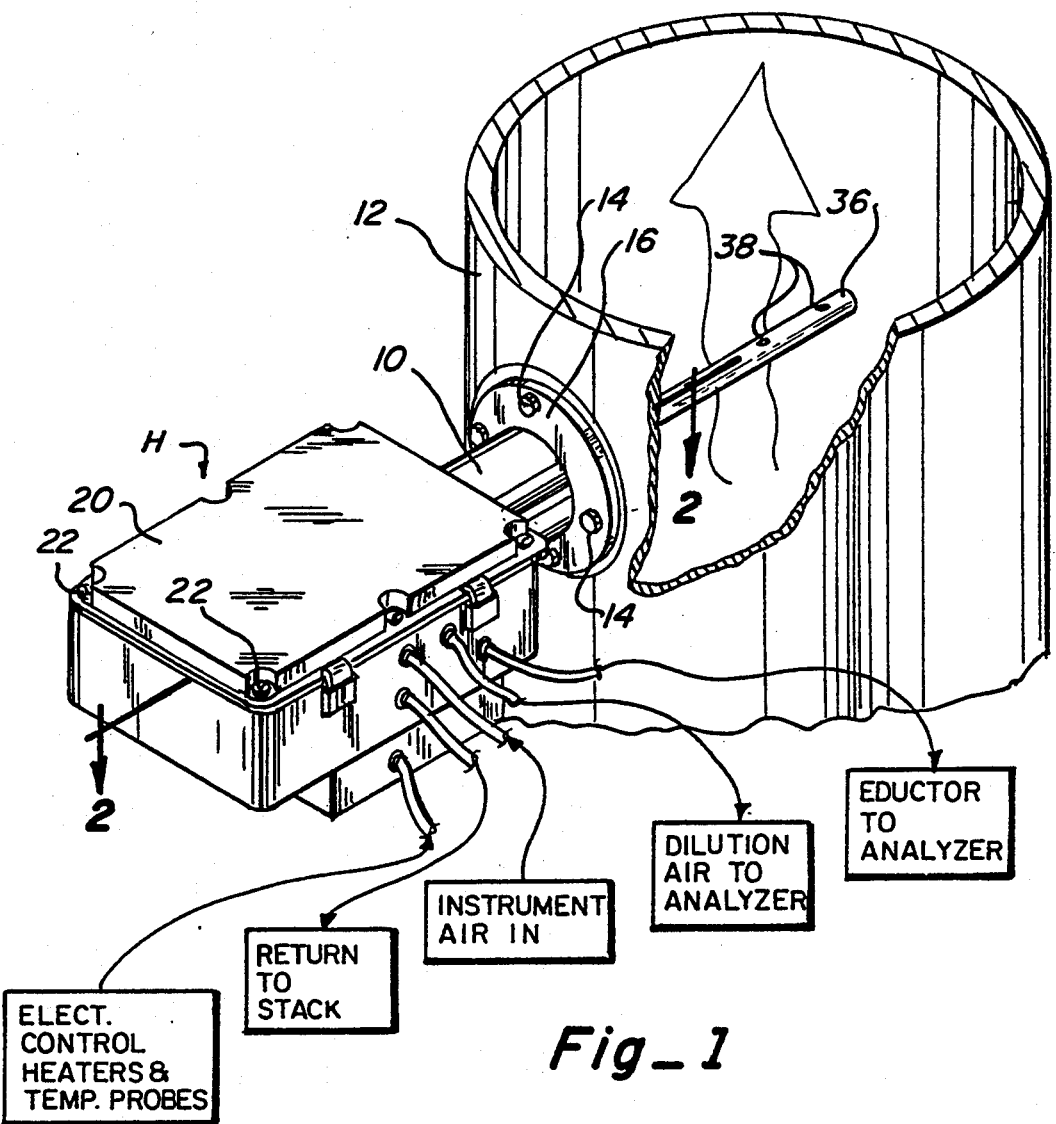
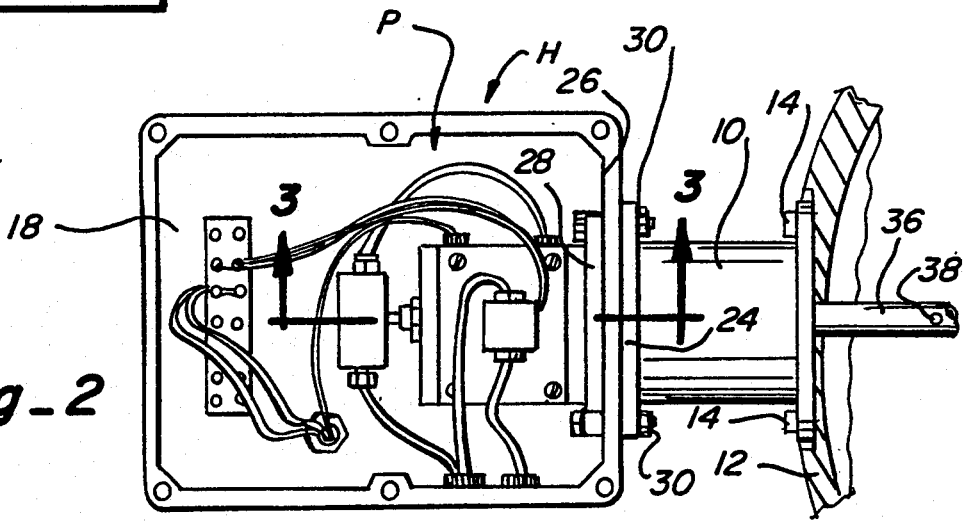

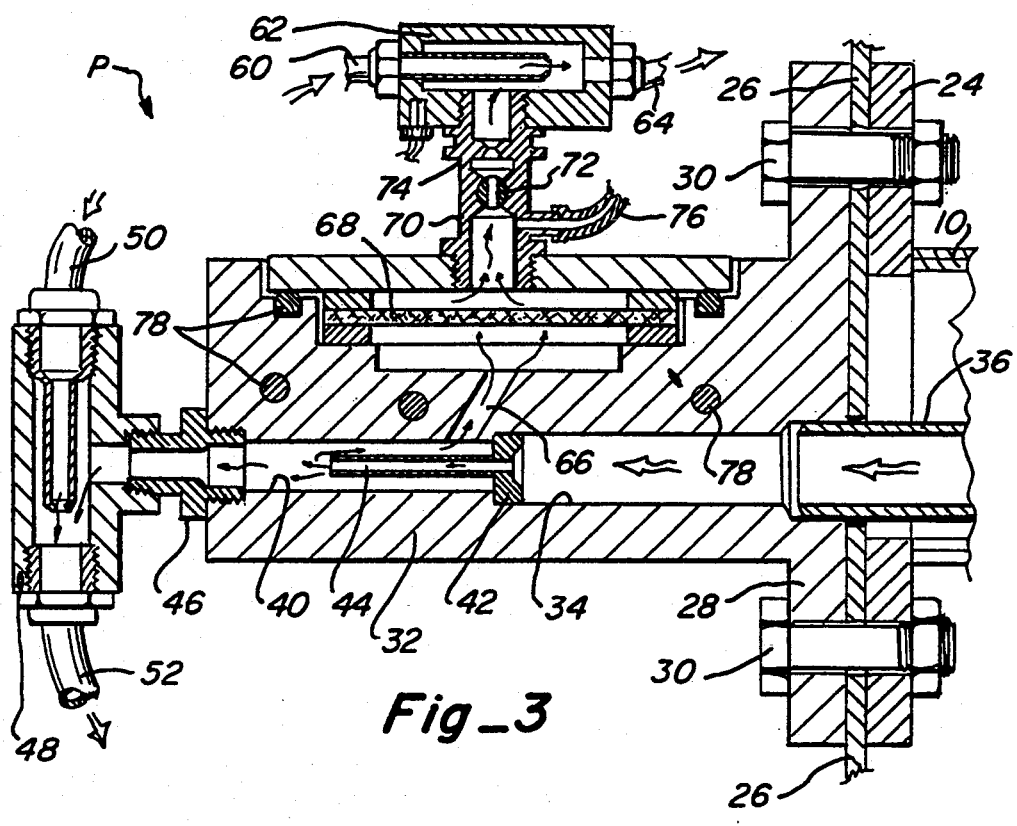
Fig_3
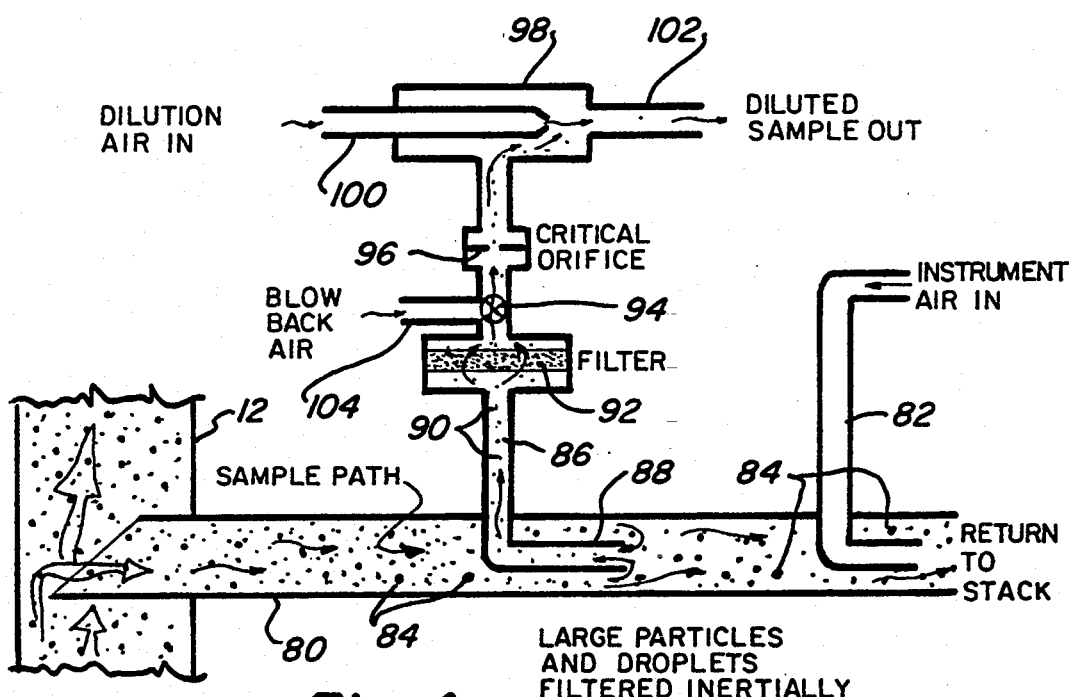
Fig_4

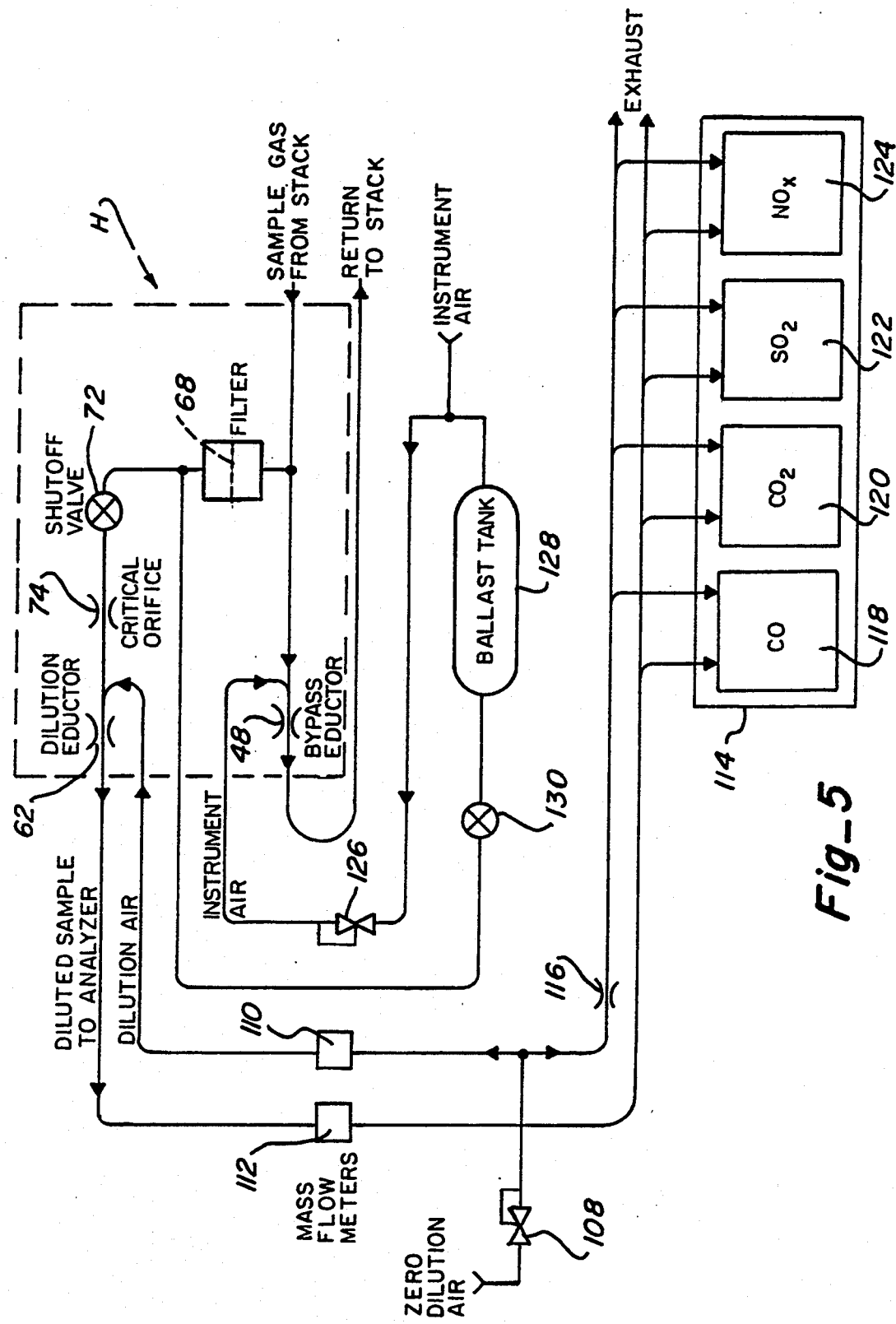
Fig_5

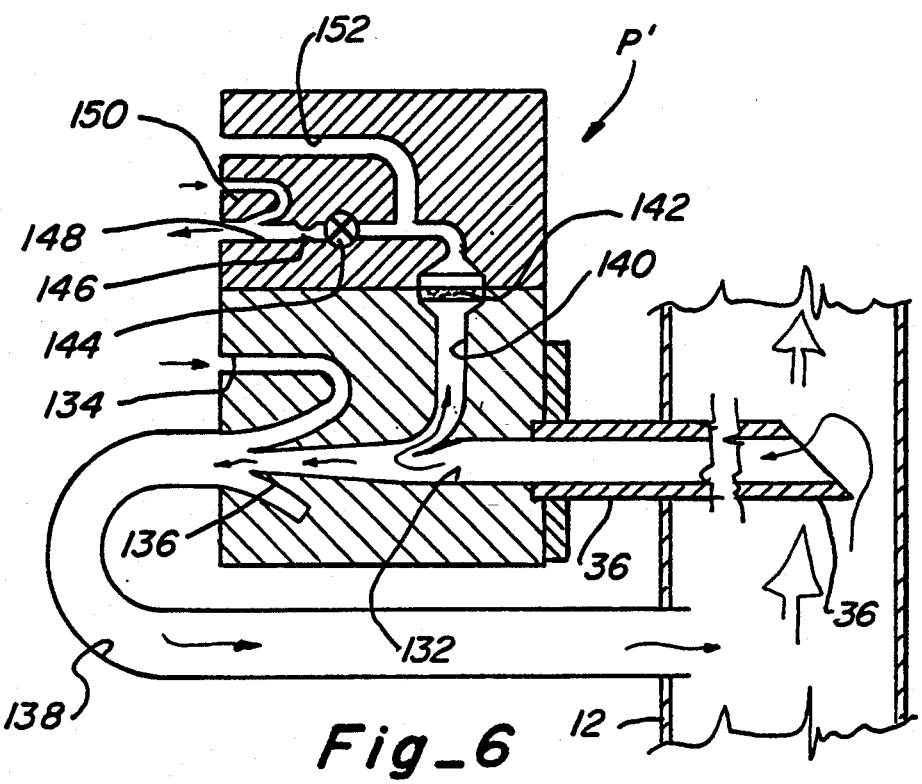
Fig_6
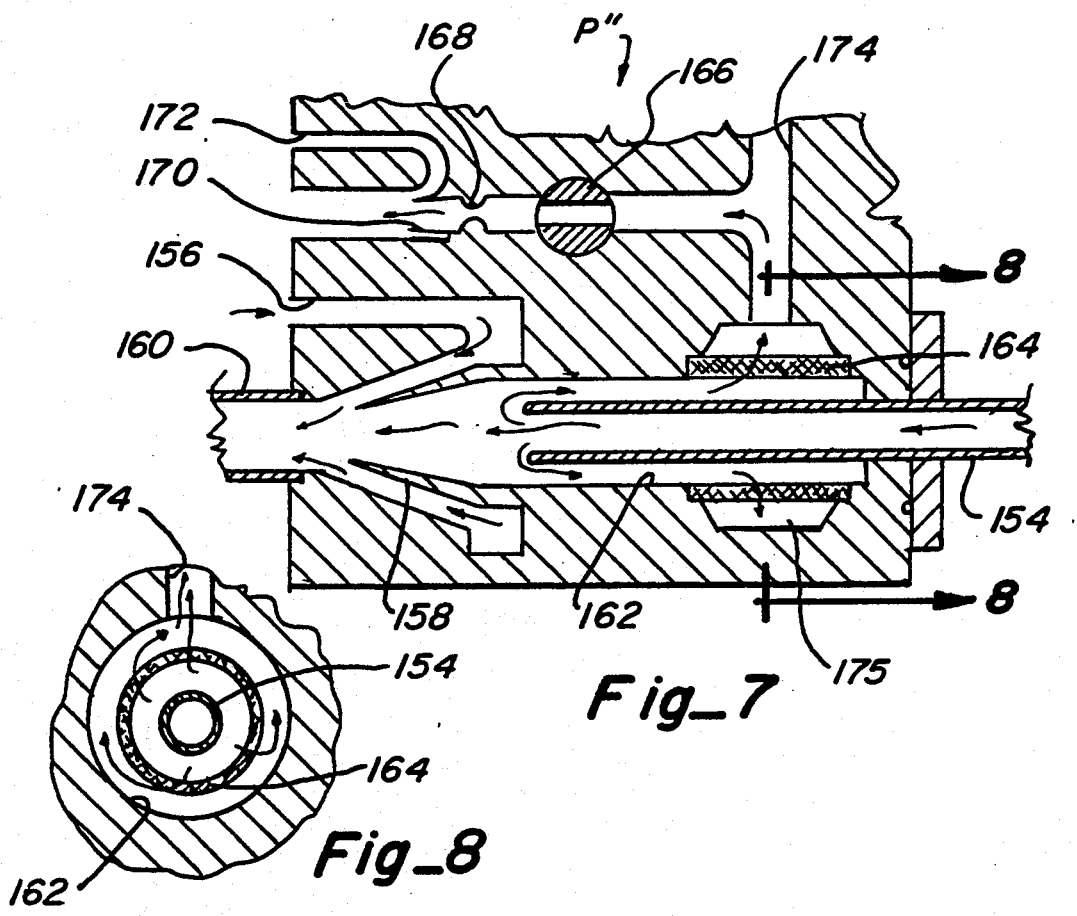
Fig_7
Fig_8

DILUTION STACK SAMPLING APPARATUS

TECHNICAL FIELD

This invention relates to a dilution probe for sampling a gas stream in a stack, and more particularly to such a probe which inertially separates most of the particulate material from the stream to extend the life of the filter and an analyzer which compares gas levels in a diluted sample with the same gas levels in the dilution air.

BACKGROUND ART

The analysis of regulated gaseous chemical compounds from smoke stacks and other industrial processes is necessary for compliance with federal, state and/or local regulations in most industrialized nations of the world. Many apparatuses have been devised to measure these compounds. These apparatuses must provide for the specific gas measurements of interest while eliminating solid particles and prevent condensation of water and other vapors which are coresident with the gas or gases of interest.

Present dilution systems suffer three important disadvantages compared to the requirements of the measurement system. First, clogging of the sample flow control element due to ineffective removal of solid and viscous matter, causes changes in the flow rate of the sample to be diluted thereby necessitating maintenance of the apparatus on a more frequent basis then desired. Secondly, dependency on the consistency of the flow control elements, typically critical orifices and/or capillary tubes, for stability of the dilution ratio over time and associated operating temperatures and other operating conditions is required. But in fact, the flow throughput does change with temperature, pressure, gas density and contamination, resulting in errors in the gas concentration measurements. Finally, certain gases to be measured are indigenous in the atmosphere. In prior art devices, indigenous compounds such as carbon dioxide and carbon monoxide must be totally removed from the air to be used for the dilution. If not, their concentrations will be added to the concentration of the sample gas which significantly complicates the analytical measurements and often yields erroneous results. Having exact knowledge, by measurement, of the actual dilution ratio is the only practical means to relate the concentration of the compounds as measured in the diluted state to the concentrations as they existed before dilution. Determination of in-process concentration is necessary for the measurement to be compliant with legal requirements.

In the prior art devices, the operator is only able to compensate for changes in the dilution by calibration with gases of known concentration. This calibration can only be done infrequently, such as daily, otherwise it will reduce the percentage of available measurement data because the apparatus can only perform one measurement at a time. In other words, no measuring is being done when the device is being calibrated. As a result, the actual dilution ratio may change between the relatively long time intervals between calibration, resulting in inaccurate process concentrations.

As the requirements for controlling pollution from smoke stacks becomes more stringent, it is important that suitable monitoring equipment be provided to minimize the effect of particulate material on the filters to minimize the necessity of cleaning them. As a result, filtration systems, which can easily be obstructed by particulate material and liquid droplets in the gas stream, must be frequently removed increasing the down-time and cost of sampling. Also, appropriate compensation for dilution ratio fluctuations is not provided. The contaminated probes cannot be cleaned easily and returned to service.

One such probe is shown in commonly assigned U.S. Pat. No. 4,974,455 to McGowan et al. This probe includes a filter which must block all entrained particulate material in the sample, requiring frequent replacement of the filter. Also, no provision is provided for compensating for the variation in flow rate do to clogging of the filter.

Other prior art dilution probes wherein the sample air from the stack passes through a filter are EPM Model 797 Dilution Probe sold by EPM Environmental, Inc. of Mount Prospect, Ill., U.S.A. and Holland Oxydan Dilution Probe manufactured by Oxydan AS of Stilling, Denmark.

DISCLOSURE OF THE INVENTION

A dilution stack sampling apparatus, for analyzing gaseous components of a gas stream containing particulate material therein is provided which has a hollow tubular probe with a first distall upstream end for receiving from a stack a sample of the gas stream, containing particulate material of varying size, to be analyzed. A passageway, has a first end communicating with the probe intermediate its ends at an angle to the probe to require a reversal in flow direction causing an inertial removal of most of the particulate material. An eductor is connected to the second end of the passageway for mixing dilution air with the sample gas for discharge from the eductor as a diluted sample. A filter is provided upstream of the second end of the passageway for removing any particulate material from the gas sample which is not removed by the inertial flow of the particulate material. Instrument air can be provided in a back-flow direction at the upstream side of the filter on a periodic basis to remove particulate material from the filter after accumulation therefrom. Various apparatus for accomplishing this purpose are described below.

A method is provided for sampling and analyzing gas, containing particulate material, from a stack which includes the steps of removing a gas sample from the stack along a first flow path, changing the flow direction of at least a portion of the gas sample to inertially remove most the particulate material from the gas sample portion, passing the gas sample portion in series through a filter, a critical orifice and an eductor, adding dilution air to the gas sample portion at the eductor to create a diluted sample, supplying the diluted sample to a gas analyzer means, measuring the rate of flow of the diluted sample to the gas analyzer means, supplying dilution gas to the gas analyzer means, measuring the rate of flow of the dilution gas to the eductor, comparing the dilution gas and the dilution sample in the gas analyzer means to determine the ratio of each measured gas in the sample to the total gas sample. In addition, a bypass eductor can be provided for removing the gas sample from the stack along the first flow path. This bypass eductor can be powered by instrument air. Excess instrument air can be stored in a ballast tank and can be used to provide periodic back-flow through the filter to remove particulate material from the filter.

With the invention just described, it is possible to provide a dilution stack sampling system wherein the filter remaining cleaner for a longer period of time because of the inertial separation of most of the particulate material from the gas sample stream. Additionally, the filter can be periodically cleaned readily by introduction of back-flow air in the reverse direction through the filter to remove any particulate material therein. Furthermore, by comparing the dilution gas and the dilution sample in the gas analyzer means it is possible to determine a ratio of each measured gas in the sample to a total gas sample.

Additional advantages of this invention will become apparent from the description which follows, taken in conjunction with the accompanying drawings.

BRIEF DESCRIPTION OF THE DRAWINGS

FIG. 1 is a perspective view of a dilution stack sampling system constructed in accordance with this invention and shown in position in a stack;

FIG. 2 is a horizontal section, taken along line 2—2 of FIG. 1, showing further details of the sampling system;

FIG. 3 is an enlarged vertical section, taken along line 3—3 of FIG. 2, showing additional details of the probe portion of the sampling system;

FIG. 4 is a diagrammatic view of a second form of the invention;

FIG. 5 is a flow diagram showing the entire dilution stack sampling system;

FIG. 6 is a section similar to FIG. 3 but showing an alternative form of the invention;

FIG. 7 is a vertical section, similar to FIG. 3 but showing a still further embodiment of the invention; and FIG. 8 is a vertical section, taken along line 8—8 of FIG. 7, showing the sample flow path through the filter.

BEST MODE FOR CARRYING OUT THE INVENTION

In accordance with one form of this invention, a dilution probe housing H is attached by means of cylindrical probe mount 10 to a stack 12 by means of bolts 14 extending through flange 16, as seen in FIG. 1. Housing H has a rectangular body 18, for containing a probe assembly P. The housing H has a lid 20 attached to body 18 by means of fastening means, such as screws 22. The housing H protects the probe assembly P from the elements and lid 20 provides access for servicing, when required. Conveniently, the opposite end of probe mount 10 has a flange 24 which abuts a wall 26 of housing 18. Probe assembly P also has a flange 28 which abuts the inside of wall 26. The flanges are joined and held in place by means of spaced bolts 30.

Flange 28 supports body 32 of probe assembly P. Body 32 has a longitudinal passageway 34 with a probe 36 attached to one end thereof for extending through probe mount 10 and into stack 12, as best seen in FIGS. 1 and 2. One or more openings 38 are provided through which gas from the stack passes into probe 36. Passageway 34 has a discharge section 40 which is of smaller diameter. A plug 42 provided at the intersection of passageway 34 and discharge section 40, has a tube 44 extending longitudinally within a portion of discharge section 40, as shown in FIG. 3. Most of the stack gas passes through passageway 34, tube 44 and discharge section 40 and out fitting 46 into eductor 48. Conveniently, instrument air introduced through tube 50 to eductor 48 and discharged through tube 52, which connects back to the stack, draws the stack gas through probe assembly P.

Typically, gases being discharged from a stack contain airborne particulate material which is drawn through probe 36 into the probe assembly. Most of the particulate matter will flow through tube 44 and discharge section 40 and then out of probe assembly P and into eductor 48 where it will be returned with the instrument gas and the stack gas back into the stack.

Advantageously, dilution air is supplied under pressure through inlet tube 60 into eductor 62 and out through outlet tube 64. This creates a low pressure area which draws sample gas in a reverse direction the stack gas as it exits from the end of tube 44. The sample gas passes through passageway 66, filter 68, conduit 70, open valve 72 and critical orifice 74 and into eductor 62 where it is mixed with the dilution air to provide a diluted sample which passes through outlet 64. Because of the change in direction that must be made by a portion of the sample gas as it exits the end of tube 44, the larger and heavier particulate material are separated inertially from the main stack gas stream and pass through fitting 46 into eductor 48 and back to the stack via discharge tube 52. Only the very small airborne particulate material that can change direction with the flow of the sample gas passes through passageway 66 to be separated out by filter 68. Thus, very little particulate material accumulates on filter 68 over any given period of time and therefore the need to clean or replace filter 68 is minimized. However, periodically back-flow air can be supplied in the form of instrument air through passageway 76. When this is done, valve 72 is closed and the back pressure air will blow air in a reverse direction through filter 68 thereby removing particulate matter from it which then passes through passageway 66 into discharge section 40 and eductor 48 back to the stack. Thus, with the novel arrangement provided by the probe assembly of this invention, as shown in the embodiment of FIG. 3, clogging of the filter by particulate material is minimized and means is provided for providing back-flow to clean the filter on a periodic basis so that the need for replacing the filter is greatly minimized. Conveniently, the body 32 of probe assembly P has heating elements 78 for maintaining the gas sample from the stack at a constant temperature.

A similar arrangement is shown diagrammatically in FIG. 4, wherein a sample is drawn from stack 12 by means of a probe 80. The flow of stack air through probe 80 is created by instrument air introduced along pathway 82 so that most of the sample gas and instrument air is returned to the stack. The large particulate material 84 in the sample path will pass from the stack through the probe 80 and back to the stack. Interposed intermediate pathway 82 and stack 12 is a sample conduit 86 having an inlet end 88 pointing in the downstream direction, as shown. Sample gas from the stack reverses direction and passes through inlet 88. However, because of the weight and size of articles 84, they continue to flow downstream and only the most minuet particles 90 enter conduit 86 where they are trapped by filter 92. The clean sample gas passes through valve 94 and critical orifice 96 into eductor 98. Dilution air is supplied to the inlet 100 of eductor 98 and passes out of the outlet 102 along with the sample gas to provide a diluted sample for evaluation. An inlet 104 is provided for back-flow air. When it is desired to clean filter 92, valve 94 is closed with respect to critical orifice 96 and eductor 98 so that the backflow air passes in a reverse direction through filter 92 removing particles 90 from it and forcing them in a reverse direction through conduit 86 into the probe 80 to be carried back to the stack.

In addition to the foregoing, the present invention provides a reliable means of extracting a precisely known quantity of stack gas, diluting it with a precisely known quantity of dry dilution air, to prevent condensation and contamination of measuring instruments, and transporting diluted sample and the dilution air, respectively, to analyzers for comparative analysis. The ratio of the flow rate of the sample to the flow rate of the dilution air plus the sample is the dilution ratio. The measured concentration of the various gases is multiplied by the inverse of the dilution ratio to compute the concentration of the compound being measured in the original sample.

The currently favored approach in the marketplace for making these measurements is a method which utilizes a dilution sample system.

In the system shown in FIG. 5, the flow rate of the dilutant gas can be measured or precisely controlled by commercially available flow meters or flow controllers. By this means the difference between the flow rate of the dilution air and the diluted gas can be measured, which is precisely the flow rate of the gas sample being extracted from the stack. With this data, the dilution ratio is continuously calculated. A digital or analog computing system or manual calculation can be performed to correct all measured data for the exact dilution ratio, thereby allowing in-process concentration to be precisely determined.

In the present invention, zero dilution air is introduced through check valve 108 and the rate of flow is measured by mass flow meter 110. A similar mass flow meter 112 is provided in the line carrying the diluted sample so that a comparison between the two measurements can be made. These gases are supplied at the rate they pass through the flow meters to gas processor 114. The dilution air passes through flow restrictor 116 to gas processor 114 and the diluted sample passes through flow meter 114 to gas processor 114. Gas processor 114 includes CO analyzer 118, $CO_2$ analyzer 120, $SO_2$ analyzer 122 and $NO_x$ analyzer 124. It will be understood that the gas processor can include additional analyzers or different analyzers than those illustrated to determine the concentration of other gases of interest.

Instrument air is supplied to eductor 48 through a check valve 126 and a ballast tank 128 is provided which has a control valve 130 for providing back-flow air through filter 68 when shut-off valve 72 is closed to clean filter 68.

Alternative probe assemblies are shown in FIGS. 6 and 7 which improve laminar flow. In this regard, a probe assembly P' in FIG. 6 draws a sample from stack 12 by probe 36. The gas passes from probe 36 through passageway 132 due to a partial vacuum created by the introduction of instrument air through duct 134 into eductor 136. Most of the stack gas moves through passageway 132 and eductor 136 and into return conduit 138 for return to stack 12. The larger and heavier particulate material will follow this flow path due to its inertial tendency to continue moving in the same direction. A portion of the stack gas will be drawn as a sample in the reverse direction through tube 140 and through filter 142, valve 144 and critical orifice 146 and through eductor 148. Only the smallest particulate material will change flow direction and pass through tube 140 to be trapped by filter 142. Air to eductor 148 is supplied through air line 150. Blow-back air can be supplied through passageway 152 for periodically cleaning filter 142 when valve 144 is closed, as previously described with respect to FIG. 3.

In the embodiment of FIG. 7, stack gas is drawn through passageway 154. Instrument air is supplied through duct 154 to eductor 158 for drawing the stack air through the tube and eductor for discharge into return conduit 160. Most of the particulate material is carried along this path. A sample of gas reverses flow around the end of passageway tube 154 and passes in a reverse direction along channel 162 and through a cylindrical filter 164, through valve 166, critical orifice 168 and eductor 170. Dilution air is supplied through air line 172 and mixes with the sample gas to provide a diluted sample for measurement. Back-flow air can be provided through passageway 174 to clean filter 164 when check valve 164 is closed, in the same manner as described in the previous embodiments. As in the previous embodiments, large and heavy particulate material will be carried through eductor 158 and return conduit 160. The very small particles will flow with the sample air along channel 162 in a reverse direction to be trapped by cylindrical filter 164 mounted in a cylindrical chamber 175 which surrounds tube 154 an is located at the end of passageway 174.

From the foregoing, several of the embodiments of the invention have been provided wherein particulate material is inertially separated from a gas sample stream so that the portion of the stream passing through the filter only has to filter out the smaller particles. Also, the flow rate of the diluted sample and the dilution air is monitored so that a comparison can be made of the gas level of the gas product being measured in each so as to precisely ascertain the amount of measured gas pollutant in the stack sample.

This invention has been described in detail with reference to particular embodiments thereof, but it will be understood that various other modifications can be effected within the spirit and scope of this invention.

We claim:

1. Dilution stack sampling apparatus for analyzing gaseous components of a gas stream containing particulate material therein, said apparatus comprising:
   a hollow probe assembly having a first distal upstream end for receiving a sample of gas from the gas stream, containing particulate material of varying size, from the stack to be analyzed and a second proximal downstream end;
   a passageway for receiving the sample of gas from the gas stream, said passageway having a first and second end, said first end communicating with said probe assembly, intermediate its ends, to cause a change in flow direction of the sample of gas to pass through said passageway to inertially remove most of the particulate material from the sample;
   means connected to said second end for mixing dilution air with the sample gas for discharge from said means as a diluted sample;
   a filter upstream of said second end of said passageway for removing the rest of the particulate matter from the sample of gas;
   said probe assembly further including:
      a body having a longitudinal channel extending therethrough, having an upstream end and a downstream end;
      a tubular probe communicating with said upstream end of said channel for receiving the sample of gas from the stack;

a tube, having an upstream end and a downstream end, mounted intermediate said ends of said channel having a smaller diameter than said channel and extending past said first end of said passageway; and a plug connected to said upstream end of said tube to mount said tube in said channel to direct downstream flow of the sample of gas through said tube in a downstream direction, a portion of the sample of gas reversing flow direction at said downstream end of said tube for reverse flow between said tube and said channel to said first end of said passageway.

2. Dilution stack sampling apparatus for analyzing gaseous components of a gas stream containing particulate material therein, said apparatus comprising:

a hollow probe assembly having a first distal upstream end for receiving a sample of gas from the gas stream, containing particulate material of varying size, from the stack to be analyzed and a second proximal downstream end;

a passageway for receiving the sample of gas from the gas stream, said passageway having a first and second end, said first end communicating with said probe assembly, intermediate its ends, to cause a change in flow direction of the sample of gas to pass through said passageway to inertially remove most of the particulate material from the sample;

means connected to said second end for mixing dilution air with the sample gas for discharge from said means as a diluted sample;

a filter upstream of said second end of said passageway for removing the rest of the particulate matter from the sample of gas;

said first end of said passageway is a cylindrical chamber surrounding said probe assembly; and said filter extends around the periphery of said chamber so that the sample gas flows past said proximal end of said probe assembly and back to said first end of said passageway and through said filter.

3. Dilution stack sampling apparatus for analyzing gaseous components of a gas stream containing particulate material therein, said apparatus comprising:

a hollow probe assembly having a first distal upstream end for receiving a sample of gas from the gas stream, containing particulate material of varying size, from the stack to be analyzed and a second proximal downstream end;

a passageway for receiving the sample of gas from the gas stream, said passageway having a first and second end, said first end communicating with said probe assembly, intermediate its ends, to cause a change in flow direction of the sample of gas to pass through said passageway to inertially remove most of the particulate material from the sample;

means connected to said second end for mixing dilution air with the sample gas for discharge from said means as a diluted sample;

a filter upstream of said second end of said passageway for removing the rest of the particulate matter from the sample of gas; and a conduit extending through at least a portion of said apparatus having a diameter greater than said proximal end of said probe assembly, said probe assembly being mounted concentrically therein, said first end of said passageway being in communication with said conduit between said ends of said probe assembly so that a portion of said sample gas flows around said proximal end of said probe assembly and reverses direction and flows back through said first end of said passageway.

* * * * *